(12) United States Patent
Andersen

(10) Patent No.: US 7,344,521 B2
(45) Date of Patent: Mar. 18, 2008

(54) OSTOMY APPLIANCE WITH A FILTER OUTLET OPENING COVERED BY A FLAP

(75) Inventor: Birthe Vestbo Andersen, Marietta, GA (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 10/502,798

(22) PCT Filed: Feb. 3, 2003

(86) PCT No.: PCT/DK03/00065

§ 371 (c)(1),
(2), (4) Date: May 27, 2005

(87) PCT Pub. No.: WO03/065945

PCT Pub. Date: Aug. 14, 2003

(65) Prior Publication Data

US 2005/0240163 A1   Oct. 27, 2005

(30) Foreign Application Priority Data

Feb. 5, 2002   (DK) ............................... 2002 00170

(51) Int. Cl.
*A61F 5/44* (2006.01)
(52) U.S. Cl. ...................... 604/332; 604/327
(58) Field of Classification Search ......... 604/322–345
See application file for complete search history.

(56) References Cited

U.S. PATENT DOCUMENTS

| | | | |
|---|---|---|---|
| 4,367,732 A | | 1/1983 | Poulsen |
| 4,411,659 A | * | 10/1983 | Jensen et al. ............... 604/332 |
| 4,449,970 A | * | 5/1984 | Bevan et al. ............... 604/333 |
| 4,451,258 A | * | 5/1984 | Jensen ......................... 604/333 |
| 4,938,749 A | * | 7/1990 | Jensen ......................... 604/333 |
| 5,051,259 A | | 9/1991 | Olsen |
| 5,401,264 A | * | 3/1995 | Leise, Jr. ..................... 604/333 |
| 5,626,569 A | * | 5/1997 | Holtermann et al. ........ 604/333 |
| 5,690,621 A | * | 11/1997 | Canela ......................... 604/333 |
| 5,693,035 A | * | 12/1997 | Leise et al. ................. 604/333 |
| 5,714,225 A | | 2/1998 | Hansen |
| 5,800,415 A | | 9/1998 | Olsen |
| 6,007,525 A | * | 12/1999 | Martell ........................ 604/333 |

(Continued)

FOREIGN PATENT DOCUMENTS

EP   0 535 801   4/1993

(Continued)

*Primary Examiner*—Michele Kidwell
(74) *Attorney, Agent, or Firm*—Jacobson Holman PLLC

(57) ABSTRACT

An ostomy appliance having a front wall and a rear wall of flexible material forming a bag, the rear wall having an inlet opening into the bag by which waste material can enter the bag, at least one of the walls having a vent through which gas may escape from the bag, a filter covering the vent and having an outlet opening, and a flap sealed at only one end thereof to the wall so as to be pivotally movable in the plane of the wall from a first position in which the flap is attached to the wall and covers the outlet opening, to a second position in which the flap is shifted to one side so as to be offset from the first position such that the filter outlet opening is at least partially open.

24 Claims, 6 Drawing Sheets

U.S. PATENT DOCUMENTS

| | | | |
|---|---|---|---|
| 6,015,399 A | 1/2000 | Mracna | |
| 6,207,873 B1* | 3/2001 | Huston | 602/41 |
| 6,328,719 B1* | 12/2001 | Holtermann et al. | 604/332 |
| 2005/0015065 A1* | 1/2005 | Falconer | 604/335 |

FOREIGN PATENT DOCUMENTS

| | | |
|---|---|---|
| EP | 0 985 390 | 3/2000 |
| GB | 2 202 746 | 10/1988 |
| GB | 2 270 265 | 3/1994 |
| GB | 2 351 237 | 12/2000 |
| GB | 2 371 487 | 7/2002 |
| WO | 91/01118 | 2/1991 |
| WO | 91/01119 | 2/1991 |
| WO | 94/18919 | 9/1994 |

* cited by examiner

OSTOMY APPLIANCE WITH A FILTER OUTLET OPENING COVERED BY A FLAP

This is a nationalization of PCT/DK03/00065 filed Feb. 3, 2003 and published in English.

BACKGROUND OF THE INVENTION

1. Field of the Invention

The present invention relates to an ostomy appliance comprising a deodorising filter, in particular ostomy bags.

In connection with surgery for a number of diseases in the gastrointestinal tract a consequence is, in many cases, that the patient is left with a stoma such as a colostomy, an ileostomy or an urostomy in the abdominal wall for the discharge of the effluents or waste products of the body, which are conveyed through the colon, the ileum or the ureter. The discharge of visceral contents including intestinal gases cannot be regulated at will, and for that purpose the opening may be closed with a closure means, e.g. a tampon or a magnetic closure, or the patient will have to rely on an appliance to collect the material emerging from such opening in the form of a receiving bag which is later emptied and/or discarded at suitable times.

Ostomy appliances are well known. Such appliances may be two-piece or one-piece appliances. In both types of appliances, an adhesive wafer is attached to the wearer's skin. In case of a one-piece appliance, a receiving member or bag is attached to the adhesive wafer. In case of a two-piece appliance, the adhesive wafer forms part of a body side member and a receiving bag is attached releasably to the body side ostomy member for receiving exudates from the stoma.

When using one-piece appliances, the whole appliance, including the adhesive skin barrier securing the appliance to the skin is normally removed and replaced by a fresh appliance. When using two-piece appliances, the body side member is left in place up to several days, and only the receiving bag attached to the body side member is replaced.

The discharge of flatus, measured in volume, may exceed the discharge of solid and liquid faecal matter by many hundred percent and therefore there is usually the need for the continuous or frequent venting of the intestine or the collecting bag. Normally the flow of flatus is deodorised with a suitable filter. Commonly the active filter is powdered active carbon, which absorbs $H_2S$ being the principal component of the smell of flatus.

In connection with the use of filters there is often a well-known need of measures for effectively preventing blocking of the inlet opening of filters of ostomy appliances. When the inlet opening of the filter is blocked, the gas discharged into the ostomy appliance cause ballooning of the bag being highly undesirable for several reasons.

Ballooning will be embarrassing for the user as the bag will bulge and there is an increased risk of leakage being unacceptable for the user.

However, it has been found in practice that for some ostomates having a very low production of flatus there is a considerable risk that air is vented more quickly from the bag through the filter than the discharge of gas into the bag and hence, a vacuum-like condition is produced in the bag. The consequence may be that due to adhesion between the walls of the receiving bag there is a considerable risk that visceral contents reaching the opening of the stoma will not immediately be able to separate the walls and "fall" into the bottom of the receiving bag but will rather stay and block the entrance to the bag. This situation is highly undesirable as faecal matter may be pressed against the area around the stoma and even beneath the adhesive wafer securing the ostomy appliance to the abdominal wall creating a risk of leakage and having aggressive influence on the skin, or even upwards against the inlet opening of a filter of the bag which will again further increase the risk of blocking of the inlet of the filter which again may result in ballooning and even leakage.

2. Description of the Related Art

At present an ostomate may try to avoid this situation using commercially available separate adhesive labels that may be applied so as to cover the outlet opening of the filter partly or fully. These separate filter labels are, however, not 100% sealing as their primary function is to protect the filter against influence of water while bathing and furthermore, such a label can only be used once. Thus, the ostomate must always carry a minor supply of labels in order to secure the collecting bag against blocking as it is always necessary from time to time to vent the bag in order to avoid ballooning.

European Patent No. EP 0 535 801 discloses an ostomy bag which has two vents one of which is filtered and the other of which is unfiltered. An adhesive strip is used to seal the vents and can be peeled back to open them so that by pulling the walls of the bag apart, air is drawn into the bag. The vent is then closed to trap air in the bag and keep the front wall away from the rear wall in the region of the opening in order to avoid "pancaking".

Published European Patent Application No. EP 0 985 390 discloses an ostomy appliance having a filtered vent having a plurality of apertures and adhesive sticker means which can be positioned to selectively expose or cover one or more of the plurality of outlets to control the flow rate through the vent. The sticker means may consist of a number of separate sticker segments which can be peeled away to selectively expose one or more exits under each segment. EP 0 985 390 is silent with respect to a sticker having a surface which may be sealed releasably to the wall enabling a placing of the sticker covering the outlet opening to a desired degree and also enabling a detachment and reattachment of the sticker according to the need which renders it possible to adapt the outlet of gas from the bag according to the actual need by relocating the sticker so as to cover more or less of the outlet vent without being dependent on disposable closures.

Thus, there is still a need of a closure which may prevent pancaking by allowing a 100% sealing of the outlet opening of the filter of an ostomy appliance and, at the same time, giving the option of allowing a minor amount of gas to pass out of an ostomy appliance according to need without having to rely on the presence of a supply of disposable closures which may only be used once and which must be disposed of in an acceptable manner.

SUMMARY OF THE INVENTION

The invention relates to an ostomy appliance comprising a front wall and a rear wall of flexible material forming a bag, the rear wall having an inlet opening into the bag by which waste material can enter the bag and at least one of the walls having one or more vents through which gas may escape from the bag and having a filter covering said vent and having an outlet opening, wherein the appliance is provided with a flap having a surface being sealable to the wall in a manner in which the flap covers the outlet opening and furthermore being sealable to the wall in a manner in which the flap is shifted sideways leaving the outlet opening of the filter partly or fully open.

The invention further relates to a device for controlling the venting of gas from an ostomy appliance and to a method of controlling the venting of gas from an ostomy appliance in order to prevent "pancaking" of the ostomy appliance and, at the same time, giving the option of allowing a minor amount of gas to pass out of the ostomy appliance according to need to avoid ballooning.

BRIEF DESCRIPTION OF THE DRAWINGS

The invention is disclosed more in detail with reference to the drawings in which.

DETAILED DESCRIPTION OF THE PRESENT INVENTION

Figure 1:
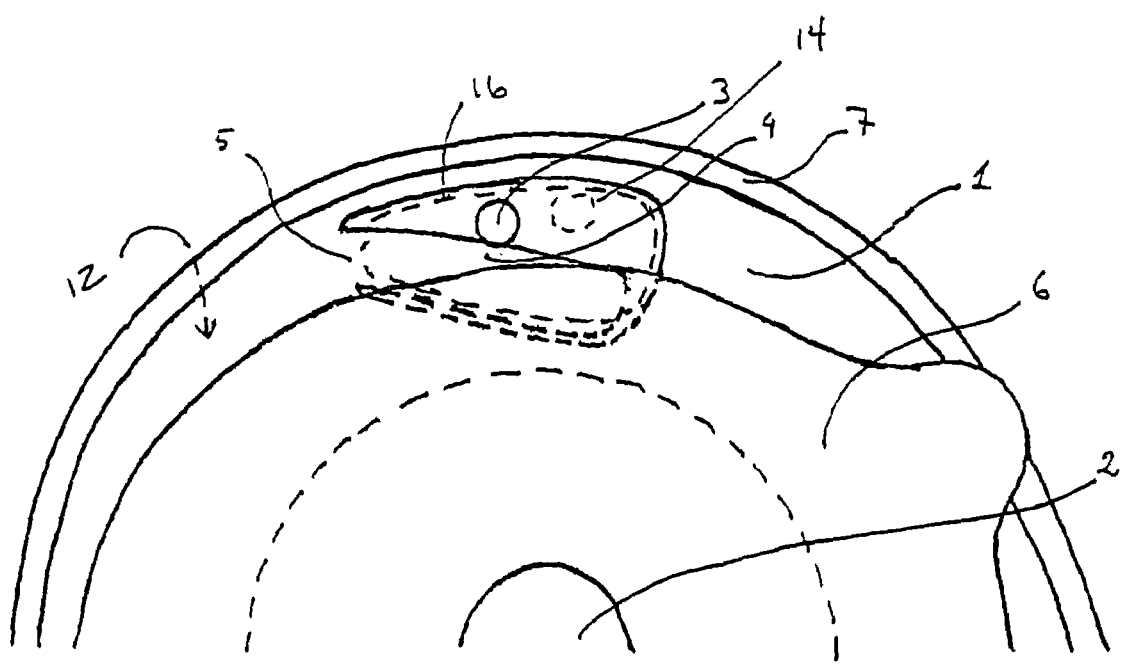
FIG. 1 shows a section of an embodiment of an appliance of the invention having a controlling device of the invention in the open state, seen from the side of the wall having a vent.

The present invention relates to an ostomy appliance comprising a front wall and a rear wall of flexible material forming a bag, the rear wall having an inlet opening into the bag by which waste material can enter the bag and one of the walls having one or more vents through which gas may escape from the bag and having a filter covering said vent and having an outlet opening, wherein the appliance is provided with a flap having a surface being sealable to the wall in a manner in which the flap is covering the outlet opening of the filter and furthermore to be a sealed to the wall in a manner wherein the flap is shifted to the side so that outlet opening of the filter is partially or fully open which appliance is characterised in that wherein one end of the flap is sealed to the wall in a manner allowing a pivoting of the flap in the plane of the wall and that the flap has a surface which may be releasably sealed to the wall.

In a preferred embodiment of the invention, the flap is provided with a hole of at least the same diameter as the outlet opening of the filter and said flap being secured to the wall in a flexible manner allowing the surface of the flap to be sealed to the wall in a manner in which the hole of the flap is aligned with the outlet opening of the filter and furthermore to be a sealed to the wall in a manner wherein the hole of the flap is shifted to the side so that outlet opening of the filter is sealed partially or fully. This embodiment is preferably delivered from the manufacturer in a condition in which the hole of the flap is aligned with the outlet opening of the filter enabling the user to obtain the benefit of the present invention and, at the same time, enables a conventional use of the ostomy appliance.

The hole may be circular or elongated such as rectangular or oval giving the options of a finer controlling of the flow according to the actual need. The longest dimension of such elongated hole is preferably in the general direction of shifting the flap.

It is also contemplated that the hole may have other shapes such as keyhole or triangular shape.

The ostomy appliance of the invention allows a 100% sealing of the outlet opening of the filter of an ostomy appliance and, at the same time, gives the option of allowing a minor amount of gas to pass out of an ostomy appliance according to need and the sealing flap may be positioned and repositioned several times eliminating the need of handling a number of disposable closures. It is preferred that the area of the wall around the outlet opening of the filter is provided with a surface layer having a surface prepared for repeated attachment and detachment of an adhesive surface and that the surface of the flap fading the wall is provided with an adhesive being suitable for safe attachment of the flap to the surface enabling a temporary venting of the bag and resealing according to need during the service time of the bag. The surface layer may e.g. be glued or welded to the wall.

The surface layer and the flap may for example be moulded in a water-repellent cellular plastics material, such as ethylene vinyl acetate (EVA) or polyurethane (PUR), preferably with closed cells so that the cellular plastic material does not absorb liquid; or be made from a suitable plastics material such as the materials suitable for production of ostomy appliances. It only has to be ensured that the force needed for peeling the flap from the adhesive is greater that the force needed for peeling the adhesive from the surface layer.

The fact that the end of the flap is sealed to the wall in a manner allowing a pivoting of the flap in the plane of the wall enables a simple means for partially sealing the outlet opening in accordance with the actual need of venting.

The flap of the ostomy appliance of the invention suitably comprises a backing layer, optionally a carrier layer for the adhesive, and an adhesive layer.

In a preferred embodiment of the invention the backing layer is an integrated part of a woven or non-woven outer layer of the appliance enabling a simple securing of the flap to the appliance. Using this embodiment it is simple to provide the pivoting as the flap may be cut having a considerable length which, combined with the pliability of the woven or non-woven layer, will allow a considerable displacement of the end of the flap in the plane of the wall.

In another embodiment of the invention the carrier layer of the flap and the surface layer of the wall are integrated and united having a connecting zone forming a hinge. This embodiment is especially suitable for use in connection with ostomy appliances not having an outer layer of woven or non-woven material or appliances for a simple enabling of the present invention.

A simple manner of achieving this is by enabling a pivoting in case of a hinged flap to have a zone of bending in which the length of the connection between the two parts is considerably smaller than the width of the flap. The length of such a zone may e.g. be from 2 to 10 millimeters, more preferred from 3 to 6 millimeters, depending of the strength and flexibility of the material of the flap.

The ostomy appliance according to the invention may be adapted for use together with an ostomy body side member (2-piece appliance) wherein the receiving bag is provided with coupling means for releasable securing to matching coupling means placed on the ostomy body side member and wherein the inlet opening is adapted for alignment with a hole of the ostomy body side member for receiving a stoma.

The ostomy appliance according to the invention may, as an alternative, be adapted for use directly (1-piece appliance) in which case the bag is provided with an adhesive wafer for securing the receiving bag to the user's skin, said bag and wafer having an inlet opening for receiving a stoma.

As indicated above, an ostomy-receiving bag of the invention is provided with a vent. Such bags may be closed bags but it is also contemplated that an ostomy-receiving bag of the invention may be in the form of an open bag.

The ostomy appliance itself comprising front and rear walls sealed together along the rim and provided with an inlet opening may be made in analogy with and from materials conventionally used for the preparation of ostomy appliances.

Such materials are suitably films composed of any suitable material, which is heat sealable and sufficiently impervious for unpleasant odours such as polyolefin films or combinations of such films, e.g. polyethylene or a coextrudate of polyethylene and polyvinylidene chloride.

An ostomy body side member for use together with an ostomy-receiving bag according to the invention may be produced from standard materials normally used for preparation of disposable ostomy and wound care and incontinence devices.

Thus, the adhesive wafer for a body side member or of a 1-piece ostomy appliance bag according to the invention may be made from a medical grade barrier adhesives known in the such as the formulation being disclosed, for example in U.S. Pat. Nos. 4,367,732, 5,051,259 or 5,714,225. For a 2-piece ostomy appliance according to the invention the body side member and the receiving bag are provided with matching coupling means.

The coupling means for use in connection with the present invention may be any suitable coupling means known per se for coupling of ostomy base plates to ostomy collecting bags, e.g. a mechanical coupling such as matching coupling rings such as the coupling rings disclosed in WO 91/01118 and WO 91/01119 or WO 94/18919 or matching flanges for adhesive connection of the type disclosed in U.S. Pat. No. 5,800,415.

Suitable materials for use as woven or non-woven outer layer are moisture resistant woven or non-woven sheet materials, which may be united with materials conventionally used in the production of ostomy appliances. Such materials are preferably compatible with the materials used for the preparation of ostomy appliances allowing a simple assembling using welding e.g. using heat, laser or high frequency welding. Preferred materials for use in the present invention are woven or non-woven materials of polyethylene, polypropylene or a polyester, which are thermoformable and may easily be welded to the wall of the bag using conventional techniques.

Preferred materials for use as surface layers for walls of appliances of the invention are sheet materials of the kinds mentioned above which may be united with materials conventionally used in the production of ostomy appliances.

The adhesive used for adhering the flap to the wall may be any suitable adhesive and is preferably an adhesive also having wet tack properties in order to ensure a proper function also in a humid environment, e.g. when bathing, which will prolong the expected service time of the appliance as an incidental wetting would not compromise the adhesiveness.

In a second aspect the invention relates to a device for controlling the venting of gas from an ostomy appliance comprising a front wall and a rear wall of flexible material forming a bag, the rear wall having an inlet opening into the bag by which waste material can enter the bag and at least one of the walls having one or more vents through which gas may escape from the bag and having a filter covering said vent and having an outlet opening, said device being in the form of a flap being secured to the wall in a manner in which the flap is covering the outlet opening of the filter and furthermore to be a sealed to the wall in a manner wherein the flap is shifted to the side so that outlet opening of the filter is partially or fully open which device is characterised in that one end of the flap is sealed to the wall in a manner allowing a pivoting of the flap in the plane of the wall and that the flap has a surface which may be releasably sealed to the wall.

The device of the invention enables a control of the venting of gas from an ostomy appliance having one or more vents through which gas may escape from the bag and having a filter covering said vent and having an outlet opening and enables prevention of "pancaking" of the ostomy appliance for ostomates having a very low production of flatus having a considerable risk that a vacuum-like condition is produced in the bag due to air being vented more quickly from the bag through the filter than the discharge of gas into the bag by enabling a total closure of the outlet opening and, at the same time, giving the option of allowing a minor amount of gas to pass out of the ostomy appliance according to need to avoid ballooning.

In a third aspect the invention relates to a method of controlling the venting of gas from an ostomy appliance for preventing "pancaking" of the ostomy appliance and, at the same time, giving the option of allowing a minor amount of gas to pass out of the ostomy appliance according to need to avoid ballooning comprising applying an ostomy appliance comprising a front wall and a rear wall of flexible material forming a bag, the rear wall having an inlet opening into the bag by which waste material can enter the bag and at least one of the walls having one or more vents through which gas may escape from the bag and having a filter covering said vent and having an outlet opening, wherein the appliance is provided with a flap being sealable to the wall in a manner in which the flap is covering the outlet opening of the filter and furthermore to be a sealed to the wall in a manner wherein the flap is shifted to the side so that outlet opening of the filter is partially or fully open, which method is characterised in that an ostomy appliance is used in which one end of the flap is sealed to the wall in a manner allowing a pivoting of the flap in the plane of the wall and that the flap has a surface Which may be releasably sealed to the wall.

DESCRIPTION OF THE PREFERRED EMBODIMENTS

The invention is now explained more in detail with reference to the drawings showing preferred embodiments of the invention. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 2:
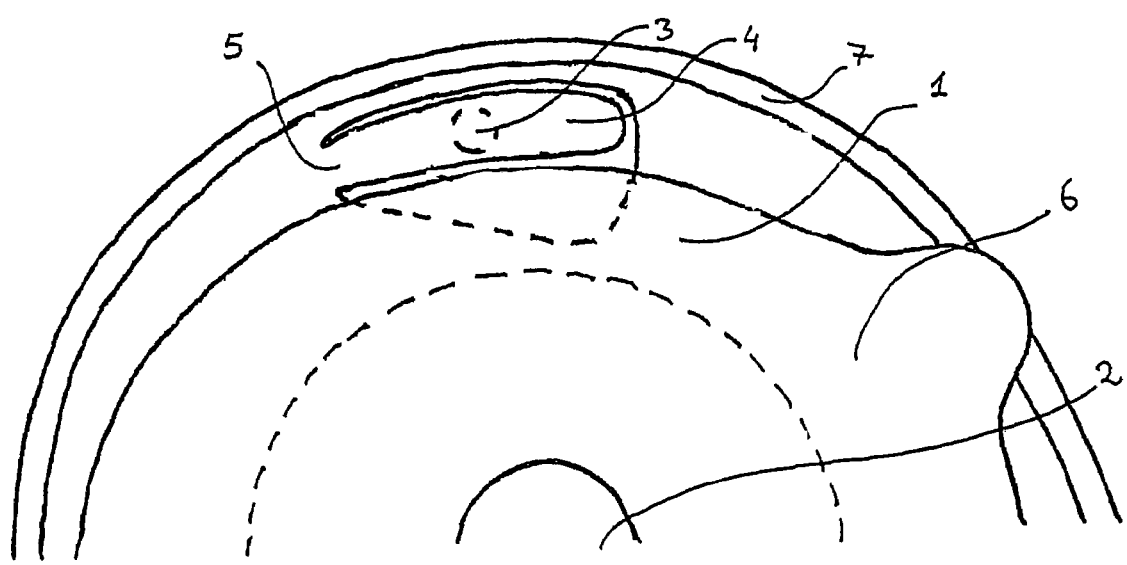
FIG. 2 shows the embodiment of FIG. 1 having the controlling device in a closed state.

Reference is made to FIGS. 1 and 2 showing a section of an embodiment of an appliance of the invention having a controlling device of the invention in the open state and closed state, respectively, seen from the side of the wall having a vent. The section shows the top of an ostomy appliance comprising a front wall 12 and a rear wall 1 of a flexible material forming a bag, the rear wall having an inlet opening 2 into the bag by which waste material can enter the bag and at least one of the walls having one or more vents 14 through which gas may escape from the bag such that a wall with a vent may be referred to herein as a vented wall. The vented wall includes a filter 16 covering the vent and having a filter outlet opening 3. The appliance is provided with a flexible flap 4 that is secured in one end 5 to the wall of the appliance and has a surface that is releasably sealable to the wall. The flap is an integrated part of a woven or non-woven outer layer of the appliance enabling a simple securing of the flap to the appliance. In this embodiment the flap is cut having a considerable length and a narrow zone at the end of the flap being secured to the bag enabling a pivoting of the flap which, combined with the pliability of the woven or non-woven layer, allows a considerable displacement of the free end of the flap in the plane of the wall of the bag for being attached to the wall either beside or covering the filter outlet opening leaving the same partly or fully open as shown in FIG. 1 or closed as shown in FIG. 2. As shown in these two figures, pivoting of the flap displaces the free end of the flap from a position beside or adjacent the filter outlet opening (FIG. 1) to a position covering the filter outlet opening (FIG. 2) such that these two positions of the flap are not concentric with one another but offset. Furthermore, FIG. 1 shows an adhesive wafer 6 for securing the appliance to the skin of the user as well as a seam 7 sealing then rims of the front and rear walls forming a bag.

Figure 3:
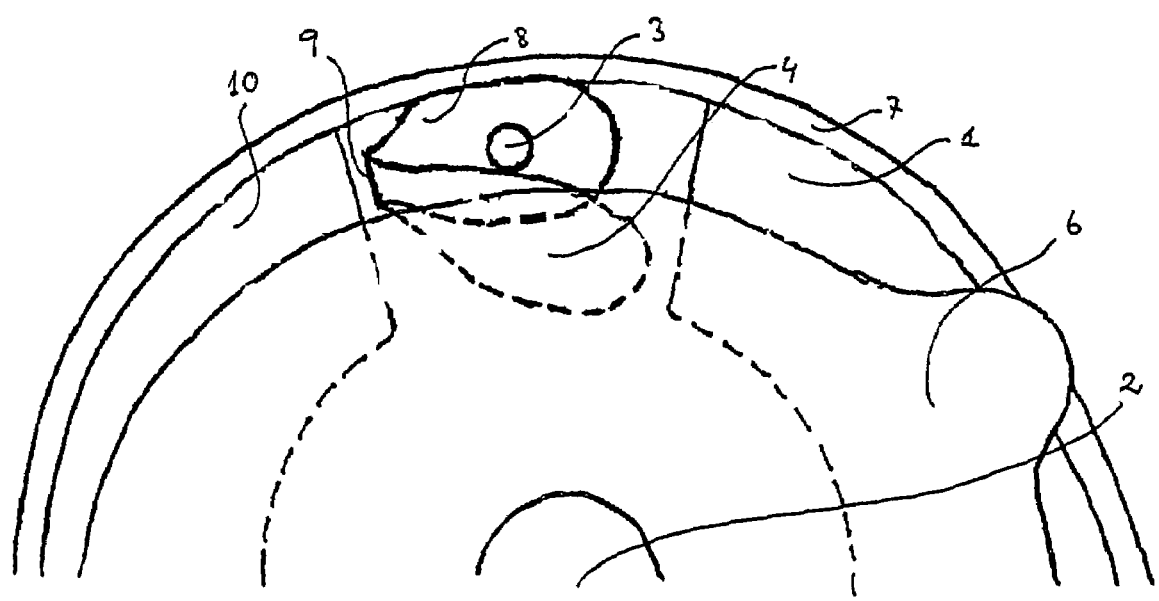
FIG. 3 shows a section of another embodiment of an appliance of the invention having a controlling device of the invention in the open state, seen from the side of the wall having a vent.
Figure 4:
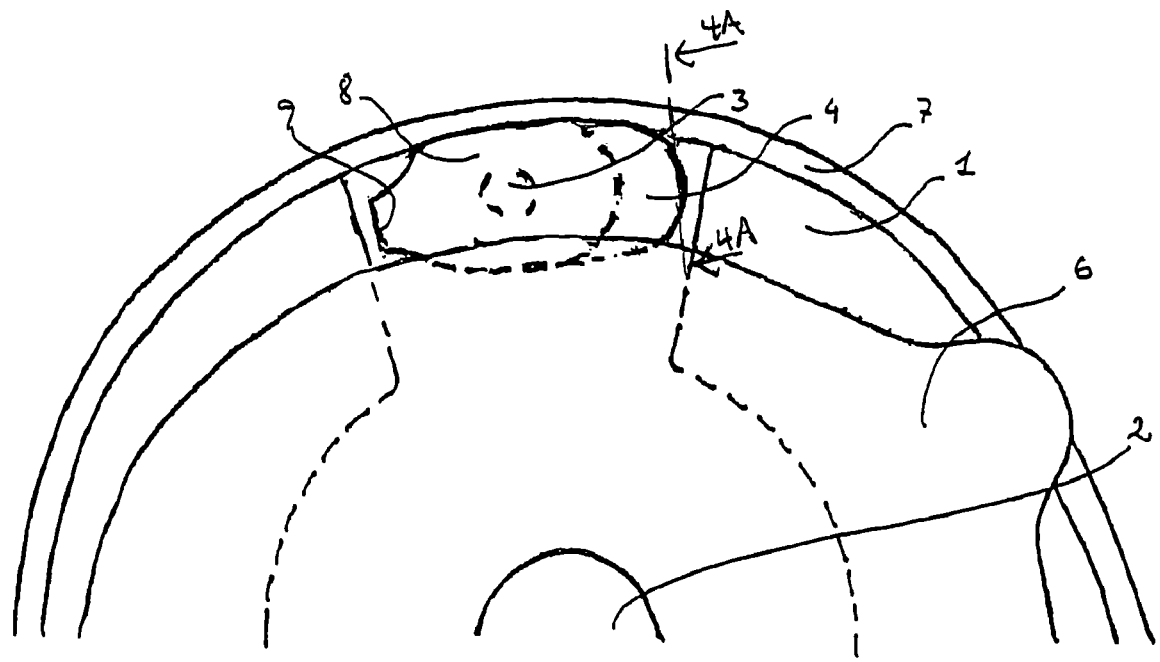
FIG. 4 shows the embodiment of FIG. 3 having the controlling device in a closed state.
Figure 4A:
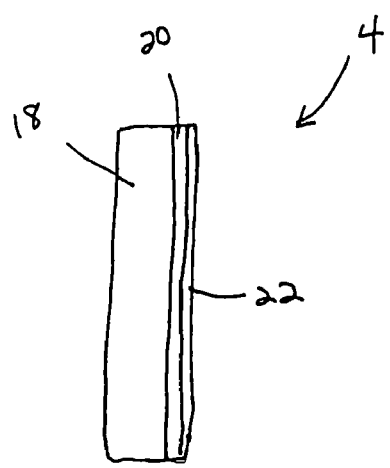
FIG. 4A is an end view of the flap taken along line 4A-4A of FIG. 4.

FIGS. 3, 4 and 4A show another embodiment of an appliance of the invention corresponding to the device shown in FIGS. 1 and 2 but having another controlling device of the invention in the open state and closed state, respectively, seen from the side of the wall having a vent. In these figures corresponding reference numbers refer to corresponding elements. In this embodiment the venting controlling device of the invention is in the form of a flap 4 having a backing layer 18, which is provided with a carrier layer 20 being integrated with a surface layer 8 placed on the wall and having a connecting zone 9 forming a hinge. The carrier layer 20 has an adhesive surface 22. In this case, a pivoting is enabled by providing a zone of bending forming the hinge in which the length of the connection between the two parts is considerably smaller than the width of the flap. Like the embodiment of FIGS. 1 and 2, the flaps pivots substantially in the plane of the wall from a position beside or adjacent the filter outlet opening (FIG. 3) to a position covering the filter outlet opening (FIG. 4) such that the two positions of the flap are not concentric with one another, but offset. In this embodiment, the bag is provided with a woven or non-woven outer layer 10 provided with an opening leaving space for the controlling device.

Figure 5:
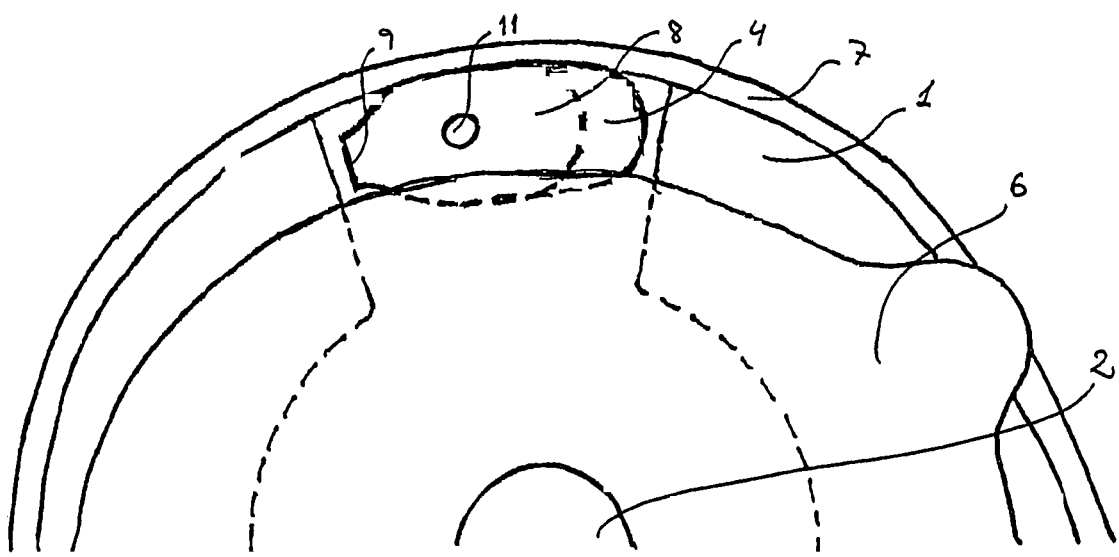
FIG. 5 shows a section of yet another embodiment of an appliance of the invention having a controlling device of the invention in the open state, seen from the side of the wall having a vent.
Figure 6:
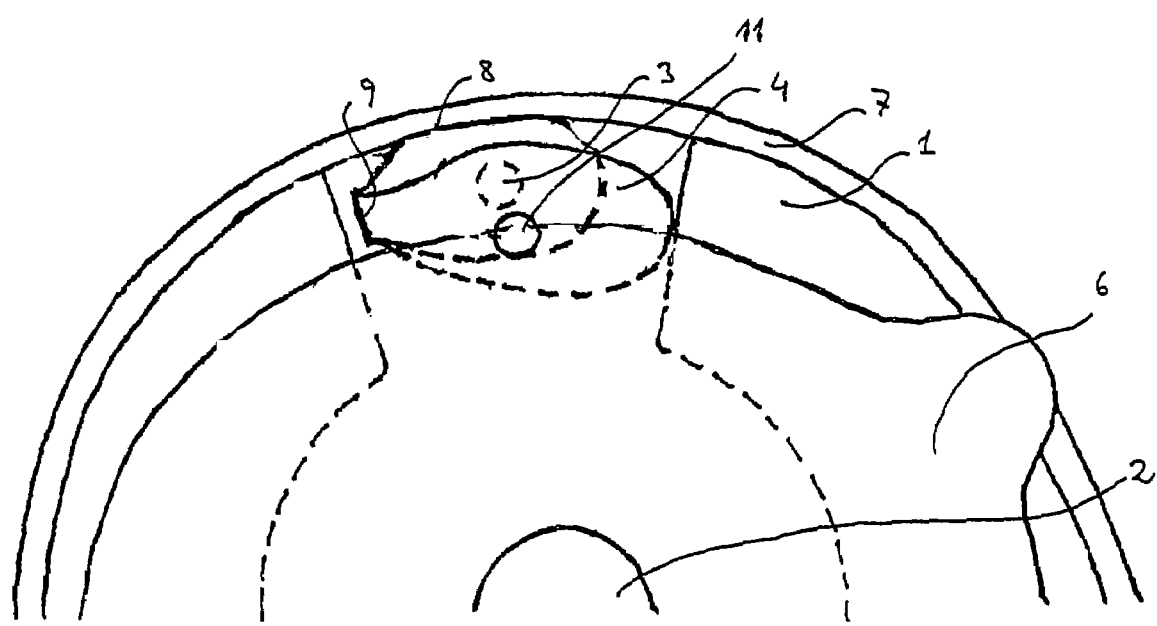
FIG. 6 shows the embodiment of FIG. 5 having the controlling device in a closed state.

FIGS. 5 and 6 show another embodiment of an appliance of the invention corresponding to the device shown in FIGS. 3 and 4 but having another controlling device of the invention in the open state and closed state, respectively, seen from the side of the wall having a vent. In these figures corresponding reference numbers refer to corresponding elements. In the embodiment shown in FIGS. 5 and 6, the flap is provided with a hole 11 of at least the same diameter as the filter outlet opening 3. The flap is secured to the wall in a flexible manner allowing the surface flap to be sealed to the wall in a manner in which the hole of the flap is aligned with the filter outlet opening of the filter and furthermore to be sealed to the wall in a manner wherein the hole of the flap is shifted to the side so that the filter outlet opening of the filter is sealed partially or fully.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. An ostomy appliance comprising a front wall and a rear wall of flexible material forming a bag, the rear wall having an inlet opening into the bag by which waste material can enter the bag, at least one of the walls of the bag having at least one vent through which gas may escape from the bag so as to be a vented wall, a filter covering said vent and having a filter outlet opening, and a flap secured at only one end thereof to said vented wall adjacent said filter outlet opening, said flap being pivotally movable between a first position in which said flap is releasably sealed to the wall and covers said filter outlet opening, and a second position in which said flap, by pivoting on said one secured end, is shifted to one side so as to be non-concentric with said first position and releasably sealed to the vented wall adjacent said filter outlet opening, said flap in said second position causing said filter outlet opening to be partially or fully open.

2. The ostomy appliance as claimed in claim 1, wherein the flap includes a hole having a diameter at least as large as a diameter of said filter outlet opening, said hole and said filter outlet opening being out of alignment when the flap is in said first position, and said hole being at least partly aligned with said filter outlet opening such that the filter outlet opening is at least partially open when the flap is in said second position.

3. The ostomy appliance as claimed in claim 1, wherein the area of the vented wall around the filter outlet opening is provided with a surface layer having a surface prepared for attachment and detachment of an adhesive surface and that a surface of the flap facing the vented wall is provided with such an adhesive.

4. The ostomy appliance as claimed in claim 1, wherein the flap includes a backing layer and an adhesive layer.

5. The ostomy appliance as claimed in claim 4, wherein said flap includes a carrier layer for the adhesive layer.

6. The ostomy appliance as claimed in claim 4, wherein the backing layer is an integrated part of a non-woven outer layer of the appliance.

7. The ostomy appliance as claimed in claim 3, wherein the flap includes a carrier layer, said carrier layer and the surface layer of the vented wall being integrated and united, having a connection zone forming a hinge.

8. The ostomy appliance as claimed in claim 1, wherein the area of the vented wall around the filter outlet opening is provided with a surface layer prepared for adhesive attachment and detachment of said flap.

9. The ostomy appliance as claimed in claim 1, wherein said flap is secured to the vented wall at a connection zone forming a hinge.

10. An ostomy appliance comprising a front wall and a rear wall of flexible material forming a bag, the rear wall having an inlet opening into the bag by which waste material can enter the bag, at least one of the walls of the bag having at least one vent through which gas may escape from the bag so as to be a vented wall, a filter covering said vent and having a filter outlet opening, and a flap secured at only one end thereof to said vented wall adjacent said filter outlet opening, said flap having a hole therein with a diameter at least as large as a diameter of said filter outlet opening, said flap being pivotally movable between a first position in which said flap is releasably sealed to the vented wall with said hole and said filter outlet opening being in alignment such that said filter outlet opening is open, and a second position in which said flap, by pivoting on said one secured end, is shifted to one side so as to be non-concentric with said first position and releasably sealed to the wall, said hole being at least partly out of alignment with said filter outlet opening such that the filter outlet opening is at least partially closed when the flap is in said second position.

11. The ostomy appliance as claimed in claim 10, wherein the flap includes a backing layer and an adhesive layer.

12. The ostomy appliance as claimed in claim 11, wherein said flap includes a carrier layer for the adhesive layer.

13. The ostomy appliance as claimed in claim 11, wherein the backing layer is an integrated part of a non-woven outer layer of the ostomy appliance.

14. The ostomy appliance as claimed in claim 10, wherein the area of the vented wall around the filter outlet opening is provided with a surface layer configured for direct attachment and detachment of said flap when releasably sealing said flap to said vented wall.

15. The ostomy appliance as claimed in claim 14, wherein said flap includes a carrier layer integrated or united with said surface layer and having a connection zone forming a hinge.

16. The ostomy appliance as claimed in claim 10, wherein said flap is secured to the vented wall at a connection zone forming a hinge.

17. A method of controlling the venting of gas from an ostomy appliance for preventing pancaking of the ostomy appliance and, at the same time, allowing a minor amount of gas to pass out of the ostomy appliance according to need to avoid ballooning, said ostomy appliance having a front wall and a rear wall of flexible material forming a bag, the rear wall having an inlet opening into the bag by which waste material can enter the bag, at least one of the walls having at least one vent through which gas may escape from the bag so as to be a vented wall, a filter covering said vent and having a filter outlet opening, and a flap secured at only one end thereof to said vented wall adjacent said filter outlet opening so as to be pivotally movable in a plane substantially parallel to the plane of the vented wall, said method comprising the steps of:
applying the ostomy appliance to an ostomate so that waste material from the ostomate's stoma can enter the bag through the inlet opening;
securing said flap in a first position in which said flap is releasably sealed to the vented wall and covers said filter outlet opening;
moving said flap in said plane substantially parallel to the plane of the vented wall to a second position in which said flap, by pivoting thereof on said one secured end, is shifted to one side so as to be offset from said first position; and
releasably sealing said flap to the vented wall in said second position, said filter outlet opening being at least partially open with said flap in said second position to allow venting of gases from said ostomy appliance.

18. The method as claimed in claim 17, wherein said step of securing said flap in the first position includes adhering an adhesive surface of said flap to a surface layer of said vented wall adjacent said filter outlet opening.

19. A method of controlling the venting of gas from an ostomy appliance for preventing pancaking of the ostomy appliance and, at the same time, allowing a minor amount of gas to pass out of the ostomy appliance according to need to avoid ballooning, said ostomy appliance having a front wall and a rear wall of flexible material forming a bag, the rear wall having an inlet opening into the bag by which waste material can enter the bag, at least one of the walls having at least one vent through which gas may escape from the bag so as to be a vented wall, a filter covering said vent and having a filter outlet opening, and a flap secured at only one end thereof to said vented wall adjacent said filter outlet opening so as to be pivotally movable, said flap having a hole therein with a diameter at least as large as a diameter of said filter outlet opening, said method comprising the steps of:
applying the ostomy appliance to an ostomate so that waste material from the ostomate's stoma can enter the bag through the inlet opening, said flap being secured in a first position in which said flap is releasably sealed to the vented wall adjacent said filter outlet opening and said hole in said flap is in alignment with said filter outlet opening such that said filter outlet opening is open to allow venting of gases from said ostomy appliance;
moving said flap to a second position in which said flap, by pivoting thereof on said one secured end, is shifted to one side so as to be non-concentric with said first position; and
releasably sealing said flap to the vented wall in said second position, said hole in said flap being at least partly out of alignment with said filter outlet opening in said second position such that the filter outlet opening is at least partially closed.

20. The method as claimed in claim 19, wherein said step of releasably sealing said flap in the second position includes adhering an adhesive surface of said flap to a surface layer of said vented wall adjacent said filter outlet opening.

21. The ostomy appliance as claimed in claim 1, wherein said flap is pivotally movable in a plane substantially parallel to the plane of said vented wall.

22. The ostomy appliance as claimed in claim 10, wherein said flap in said second position is releasably sealed directly to said vented wall or to a surface layer provided on said vented wall for releasable sealing of said flap.

23. The ostomy appliance as claimed in claim 22, wherein said surface layer is glued or welded on said vented wall.

24. The ostomy appliance as claimed in claim 1, wherein the area of the vented wall around the filter outlet opening is provided with a surface layer configured for direct attachment and detachment of said flap when releasably sealing said flap to said vented wall.

* * * * *